United States Patent [19]

Inada

[11] Patent Number: 4,582,826

[45] Date of Patent: Apr. 15, 1986

[54] METHOD OF TREATING THROMBOSIS

[75] Inventor: Yuji Inada, Tokyo, Japan

[73] Assignee: Bellex Corporation, Tokyo, Japan

[21] Appl. No.: 634,802

[22] Filed: Jul. 26, 1984

[30] Foreign Application Priority Data

Aug. 13, 1983 [JP] Japan ................. 58-148406

[51] Int. Cl.$^4$ ............................................. A61K 31/56
[52] U.S. Cl. ................................................. 514/182
[58] Field of Search ...................... 260/397.2; 514/182

[56] References Cited

U.S. PATENT DOCUMENTS 4,195,084 3/1980 Ong .................................. 260/397.4

FOREIGN PATENT DOCUMENTS 2053035 4/1971 France ............................. 260/397.4
2228493 12/1974 France ............................. 260/397.4
934686 8/1963 United Kingdom ............. 260/397.4

OTHER PUBLICATIONS

"Steroids" by Fieser et al., (1959), pp. 351, 352 and 358.
Chemical Abstracts, vol. 69, (1968), p. 7010, Abst. 75139k.
Chemical Abstracts, vol. 76, (1972), p. 255, Abst. 63155u.

*Primary Examiner*—Elbert L. Roberts
*Attorney, Agent, or Firm*—Frishauf, Holtz, Goodman & Woodward

[57] ABSTRACT

A method of treating thrombosis, which comprises administering to a living body a thrombosis preventive and curative preparation containing as an active ingredient a pharmaceutically effective amount of a plant sterol selected from the group consisting of sitosterol and fucosterol, or an ester thereof.

5 Claims, No Drawings

METHOD OF TREATING THROMBOSIS

BACKGROUND OF THE INVENTION

This invention relates to a preventive and curative preparation for thrombosis, which comprises as an active component thereof sitosterol or fucosterol which is a plant sterol containing an ethyl or ethylidene group at the 24-position, and a method of treating thrombosis.

Thrombosis causes blood to undergo localized coagulation into thrombi in blood vessels or cardiac cavities in a living body, whereby to develop circulation troubles and thus to cause serious diseases such as cerebral apoplexy and myocardial infraction. As a factor taking part in the formation of thrombi, there is an acceleration in coagulability of blood. This acceleration is observed together with increased blood platelets, enhanced aggregability of blood platelets, increased concentrations of various coagulation factors, decreased concentrations of anti-coagulation factors and of fibrinolytic substances, and so on. For the prevention and treatment of thrombosis, heparin and coumarin derivatives have been used as drugs for reducing the coagulability of blood. Besides, preparations of enzymes having plasminogen-activating effects, such as urokinase, streptokinase and the like, have been developed in recent years as thrombus resolvents which can positively dissolve thrombi and can thus improve the flow of blood. These conventional preparations are however accompanied by such problems as strong antigenicity, high pyrogenicity and short-lasting effectiveness.

Taking a hint from the fact that in the activation of fibrinolytic substances for dissolution of thrombi, plasmin which serves to solubilize fibrin is formed as a result of an action of a plasminogen-activating substance produced by vascular endothelial cells on plasminogen, the present inventor has carried out an extensive investigation on substances which may accelerate the formation of plasminogen-activating substances. As a result, it has been found that a great deal of a plasminogen-activating substance may be released from vascular endothelial cells in the presence of a plant sterol of a certain type, such as sitosterol and fucosterol, leading to completion of this invention.

Sitosterol has ever been used as an anticholesteremic as disclosed in, e.g., Chemical Abstract Vol. 82 (1975) 175227z and Chemical Abstact Vol. 93 (1980) 54004t. However, the present inventor is the first to have discovered that the sitosterol and the fucosterol or an ester of these are useful for treatment of thrombosis.

SUMMARY OF THE INVENTION

An objent of this invention is to provide a preventive and curative preparation for thrombosis.

Another object of this invention is to provide a useful method for treating thrombosis.

According to this invention, there is provided a preventive and curative preparation for thrombosis, comprising a pharmaceutically effective amount of a plant sterol selected from the group consisting of sitosterol and fucosterol, or an ester thereof, and a pharmaceutically acceptable carrier.

Also provided according to this invention is a method of treating thormbosis, which comprises administering to a living body a preventive and curative preparation for thrombosis containing as an active component a plant sterol selected from the group consisting of sitosterol and fucosterol, or an ester thereof, in an amount of from 10 to 500 mg/day as the active component.

DESCRIPTION OF THE PREFERRED EMBODIMENTS

Plant sterols each of which has an ethyl or ethylidene group at the 24-position have a basic structure of the following formula:

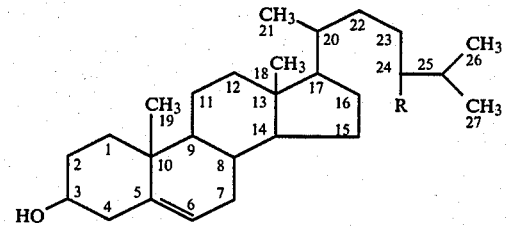

and, of these, sitosterol and fucosterol which are effective in the practice of this invention have the following their respective chracteristic structural formulae:

| Compound | Molecular formula | Structure | m.p. (°C.) |
|---|---|---|---|
| Sitosterol | $C_{29}H_{50}O$ | $R:C_2H_5$ | 137 |
| Fucosterol | $C_{29}H_{48}O$ | $R:=CHCH_3$ | 124 |

It is feasible to use esters of the above compounds, for example, their acetates, benzoates, and fatty acid esters. The above-described plant sterols per se have been known and are contained at relatively high concentrations in soybeans, wheat, cotton seeds, brown algae, and the like. They may be obtained by saponifying vegetable oils, and by methods known per se in the art, separating them out from unsaponified residues and purifying them subsequently.

The thrombosis preventive and curative preparation of this invention may be administered as an oral or parentheral preparation by using sitosterol or fucosterol, or an ester thereof, either singly or in combination with a pharmaceutically acceptable carrier. As oral preparations, may be included powders, tablets, granules, capsules, solutions, emulsions and syrups. As parentheral preparations, may be mentioned by way of example injectable preparations, infusing preparations, suppositories, etc. Illustrative of usable excipients are water, ethanol, lactose, starch, dextrin, calcium phosphate, calcium carbonate, aluminum silicate, magnesium oxide, magnesium stearate, dry aluminum hydroxide and so on.

The dosage may vary depending on the age, conditions and the like of each patient. In the case of an injectable preparation, an adult patient may be administered as the effective component at about 10 to 500 mg/day, or preferably 50 to 250 mg/day, approximately; in the case of an oral preparation, 50 to 500 mg/day, preferably 50 to 250 mg/day, approximately.

The present invention will hereinafter be described in greater detail in the following Experiments and Examples:

EXPERIMENT 1

Fresh bovine carotid arteries were obtained from a slaughter house. Endothelial cells were collected by opening the arteries lengthwise and scraping off their endothelial cell layers. In a constant-temperature 5%-CO$_2$ chamber, the thus-collected vascular endothelial cells were cultured at 37° C. in a petri dish containing an Eagle's minimum essential medium to which fetal bovine serum (10%), streptomycin (50 mcg/ml) and penicillin (50 I.U./ml) were added. The thus-cultured endothelial cells were cultured over one generation in a petri dish containing a culture medium (final ethanol concentration: 1%) which was prepared by adding a prescribed amount of a plant sterol dissolved in ethanol to the same culture medium as that used above. After cultivation, the culture medium was removed and the endothelial cells were washed with an Eagle's minimum essential medium. Thereafter, the endothelial cells were cultured at 37° C. for 6 hours in the same serum-free culture medium, thereby preparing a test solution which contained a plasminogen-activating substance secreted from the endothelial cells. The test solution was stored at −20° C.

In order to measure the plasminogen-activating activity in the test solution, a fibrin suspension was prepared in the following manner. Dissolved in a 1M NaBr-0.05M acetate buffer solution having a pH of 5.3 was 0.1 ml of a solution containing 30 μM of fibrin. In order to form fibrin clots, a liquid mixture of 2 ml of 100 g/l gum arabic, 3 ml of a 0.5M imidazole buffer solution (pH 7.5) and 25 ml of a 5 mM phosphate—0.15 M NaCl buffer solution (pH 7.5) was added. The resultant solution was subjected for 30 minutes to an ultrasonic treatment at 20 KHz to prepare a suspension containing fibrin as fine particles. The suspension was stored at 4° C.

The plasminogen-activating activity was measured in accordance with the following method. Two hundred microliters (200 μl) of the above-prepared test solution of endothelial cells were added to a liquid mixture of 700 μl of the above-prepared fibrin suspension and 100 μl of 0.7 I.U. plasminogen. The resultant mixture was maintained at 37° C. A reduction in turbidity of the fibrin suspension was measured by a nephelometer. A standard curve was drawn from a value required for a 20% reduction of turbidity in the same manner except that 0.005 to 0.08 I.U. of urokinase was used in lieu of the test solution. The plasminogen-activating activity in the test solution was expressed in terms of an urokinase unit per $1 \times 10^7$ endothelial cells by comparing its value required for the 20% reduction of turbidity with the standard curve.

Table 1 shows the plasminogen-activating activity levels of test solutions which were obtained by culturing endothelial cells, which had been cultured in the presence of 25 μM of sitosterol or fucosterol added therein, for 2, 4 and 6 hours. respectively.

TABLE 1

|  | Urokinase units/10$^7$ cells Secretion time | | |
|---|---|---|---|
|  | 2 hrs. | 4 hrs. | 6 hrs. |
| Sitosterol | 0.07 | 0.14 | 0.41 |
| Fucosterol | 0.15 | 0.35 | 0.60 |
| Control (None) | 0 | 0.03 | 0.10 |

It is understood from Table 1 that a plasminogen-activating substance was secreted abundantly more and more from endothelial cells cultured in the presence of added sitosterol or fucosterol as the culturing time increased. However, secretion of such a plasminogen-activating substance was not observed from endothelial cells cultured in the presence of added cholesterol and 5-andorosten-3β-ol in other Experiments which were conducted simultaneously with the above Experiment.

Endothelial cells were cultured by incorporating sitosterol at varied levels. The thus-cultured endothelial cell samples were individually cultured for further 6 hours to obtain test solutions. Table 2 shows the plasminogen-activating activity levels of the test solutions.

TABLE 2

| Amount of added sitosterol (μM) | Urokinase units/10$^7$ cells |
|---|---|
| 0 | 0.13 |
| 20 | 0.17 |
| 25 | 0.37 |
| 30 | 0.83 |
| 50 | 1.54 |
| 250 | 1.54 |

It is clearly shown from Table 2 that the plasminogen-activating activity was increased in the presence of 20 μM or more of added sitosterol. At high concentrations of 50 μM and up, the plasminogen-activating activity reached saturation at a level as high as about 10 times the plasminogen-activating activity of the test solution obtained without addition of sitosterol.

EXPERIMENT 2

Ten milligrams of sitosterol were dissolved in 40 μl of DMF, followed by an addition of 0.8 ml of physiological saline. Thereafter, the resulting mixture was subjected to an ultrasonic treatment to prepare a suspension. This suspension (0.8 ml) was injected in an ear vein of a female rabbit having a body weight of about 3 kg. Blood were periodically collected 2 ml by 2 ml from the ear vein. The amounts of fibrinogen and FDP, a fibrin degradation product, in the resulting serum were quantitatively analyzed respectively by a spectroscopic technique (Clin. Chem., 24, 351, 1978) and with a commercial FDP kit. Results are summarized in Table 3.

TABLE 3

| Time (hrs.) | Amount of fibrinogen (mg/ml) | Amount of FDP (μg/ml) |
|---|---|---|
| 0 | 1.6 | 1.4 |
| 3 | 1.6 | 1.4 |
| 6 | 1.3 | 12.8 |
| 26 | 1.65 | 6.4 |
| 72 | 1.70 | 3.2 |

From Table 3, it is understood that after administration of sitosterol, the amount of fibrinogen in blood decreased but the amount of FDP conversely increased, both along the passage of time, and an inversely proportional relation was established therebetween. Namely, 6 hours later, the amount of fibrinogen in blood dropped by about 20% from its normal level whereas the amount of FDP was found to be a high level of 12.8 μg/ml, 8 times its normal level. Thereafter, the amount of FDP decreased gradually from the above-mentioned level and returned to its original level upon an elapsed time of about 72 hours.

EXPERIMENT 3

In order to identify whether the production of plasminogen-activator in the cells is stimulated by other sterols, similar experiments were carried out using various kinds of sterols. Endothelial cell monolayers obtained in the medium with or without 25 μM of various sterols were washed and were incubated with serum-free medium. After incubation, conditioned media and cellular extracts were prepared and assayed in the similar manner as in Experiment 1. Among them, fucosterol remarkably enhanced the intracellular and extracellular activities of plasminogen activator. The activity was not enhanced at all by other steroids such as 20(R)-(3'-methyl)-butyl-5-pregnen-3β-ol, 20-isocholesterol, 22-dehydrocholesterol, isofucosterol and sex hormons including androsterone, testosterone, estrone and estradiol. These results are shown in Table 4.

TABLE 4

Extracellular and intracellular activities of plasminogen activator in various sterols-treated endothelial cells

| Treatment | Plasminogen-activating activity (Urokinase units/$10^7$ cells) | | |
|---|---|---|---|
| | Cellular extract after incubation for | | Conditioned media after incubation for |
| | 0 hr | 8 hr | 8 hr |
| Control | 0.08 | 0.08 | 0.32 |
| Androsterone | 0.07 | 0.08 | 0.23 |
| Estrone | 0.10 | 0.08 | 0.26 |
| Sitosterol | 0.20 | 0.20 | 0.95 |
| Fucosterol | 0.40 | 0.58 | 2.11 |

It is seen from Table 4 that the activity of plasminogen activator was enhanced 6 to 7 times in conditioned media and cellular extracts by fucosterol in comparison with control. The level of plasminogen-activating activity enhanced by fucosterol was 2 to 3 times greater than that by sitosterol. The effect of androsterone and estrone on the activity of plasminogen activator in conditioned media and cellular extracts was also shown in the table as an example of other sterols. No stimulative effect was observed with these sterols. Fucosterol itself had no fibrinolytic activity and did not directly stimulate the activity of plasminogen activator.

As apparent from the above Experiments, the thrombosis preventive and curative preparation of this invention is clearly effective in stimulating vascular endothelial cells to produce plasminogen-activating substances, causing the endothelial cells to secrete out the plasminogen-activating substances so as to activate fibrinolytic substances, and hence preventing the formation of thrombi or accelerating the dissolution of fibrin clots to cure thrombosis. The thrombosis preventive and curative preparation of this invention is superior to conventional enzyme-based preparations in that the former is free from the antigenic danger and enjoys long-lasting effectiveness.

EXAMPLE 1

One hundred milligrams of sitosterol were dissolved in ethanol. The resulting solution was poured in an ampule and sterilized, thereby obtaining an injectable preparation. When using this preparation, it should be administered in combination with an injectable solution of 0.3% lidocaine.

EXAMPLE 2

Mixed were 20 parts of fucosterol, 2.5 parts of lactose and 1 part of CMC-Na, followed by an addition of a PVA solution. The resultant mixture was formed into granules. After adding a small amount of magnesium stearate to the granules, the thus-obtained mixture was tableted to obtain tablets containing 50 mg/tablet of fucosterol.

I claim:

1. A method of treating thrombosis, which comprises administering to a living body a thrombosis preventive and curative preparation containing as an active ingredient a pharmaceutically effective amount of a plant sterol selected from the group consisting of sitosterol and fucosterol, or an ester thereof.

2. The method according to claim 1, wherein said active ingredient is administered in an amount of about 10 to about 500 mg/day.

3. The method according to claim 2, wherein said active ingredient is administered in an amount of about 50 to about 250 mg/day.

4. The method according to claim 1, wherein said plant sterol is sitosterol.

5. The method according to claim 1, wherein said plant sterol is fucosterol.

* * * * *